US009447042B2

(12) United States Patent
Kita et al.

(10) Patent No.: US 9,447,042 B2
(45) Date of Patent: Sep. 20, 2016

(54) ENDOPARASITE CONTROL AGENT

(75) Inventors: Kiyoshi Kita, Tokyo (JP); Akiyuki Suwa, Osaka (JP)

(73) Assignees: THE UNIVERSITY OF TOKYO, Tokyo (JP); NIHON NOHYAKU CO., LTD., Tokyo (JP)

( * ) Notice: Subject to any disclaimer, the term of this patent is extended or adjusted under 35 U.S.C. 154(b) by 35 days.

(21) Appl. No.: 14/000,974

(22) PCT Filed: Mar. 1, 2012

(86) PCT No.: PCT/JP2012/055190
§ 371 (c)(1),
(2), (4) Date: Oct. 14, 2013

(87) PCT Pub. No.: WO2012/118139
PCT Pub. Date: Sep. 7, 2012

(65) Prior Publication Data
US 2014/0088157 A1 Mar. 27, 2014

(30) Foreign Application Priority Data

Mar. 2, 2011 (JP) ................................. 2011-045042

(51) Int. Cl.
| | | |
|---|---|---|
| *A61K 31/18* | (2006.01) | |
| *A61K 31/44* | (2006.01) | |
| *A61K 31/166* | (2006.01) | |
| *A61K 31/4402* | (2006.01) | |
| *A61K 9/00* | (2006.01) | |
| *A61K 9/06* | (2006.01) | |
| *A61K 9/08* | (2006.01) | |
| *A61K 9/107* | (2006.01) | |
| *A61K 9/20* | (2006.01) | |
| *C07C 233/66* | (2006.01) | |
| *C07C 233/73* | (2006.01) | |
| *C07C 323/63* | (2006.01) | |
| *C07D 213/40* | (2006.01) | |
| *C07D 213/61* | (2006.01) | |
| *C07D 213/56* | (2006.01) | |
| *C07D 231/56* | (2006.01) | |

(52) U.S. Cl.
CPC ........... *C07D 213/40* (2013.01); *A61K 9/0019* (2013.01); *A61K 9/06* (2013.01); *A61K 9/08* (2013.01); *A61K 9/107* (2013.01); *A61K 9/2009* (2013.01); *A61K 31/166* (2013.01); *A61K 31/18* (2013.01); *A61K 31/44* (2013.01); *A61K 31/4402* (2013.01); *C07C 233/66* (2013.01); *C07C 233/73* (2013.01); *C07C 323/63* (2013.01); *C07D 213/56* (2013.01); *C07D 213/61* (2013.01); *A61K 9/0014* (2013.01)

(58) Field of Classification Search
CPC . C07C 233/66; C07C 233/73; C07C 232/63; A61K 31/166; A61K 31/18; A61K 31/44; A61K 31/4402; A61K 9/0014; A61K 9/0019; A61K 9/06; A61K 9/08; A61K 9/107; A61K 9/2009; C07D 213/40; C07D 213/56; C07D 213/61

See application file for complete search history.

(56) References Cited

U.S. PATENT DOCUMENTS

| | | | |
|---|---|---|---|
| 4,093,743 | A | 6/1978 | Yabutani et al. |
| 5,589,503 | A | 12/1996 | Mencke et al. |
| 6,255,333 | B1 * | 7/2001 | Banks ........................... 514/406 |
| 2005/0033081 | A1 | 2/2005 | Ducray et al. |
| 2010/0048647 | A1 | 2/2010 | Suwa |
| 2010/0249193 | A1 | 9/2010 | Andersch et al. |
| 2011/0136831 | A1 | 6/2011 | Oda et al. |

FOREIGN PATENT DOCUMENTS

| | | |
|---|---|---|
| EP | 0314422 A2 | 5/1989 |
| EP | 1997800 A1 | 12/2008 |
| JP | S53-9739 A | 1/1978 |
| JP | H01-151546 A | 6/1989 |
| JP | 2005-511685 A | 4/2005 |
| WO | WO-0249641 A2 | 6/2002 |
| WO | WO-03048112 A1 | 6/2003 |
| WO | WO-2004016088 A2 | 2/2004 |
| WO | WO-2007060162 A1 | 5/2007 |
| WO | WO-2007/108483 A1 | 9/2007 |
| WO | WO-2008003745 A1 | 1/2008 |
| WO | WO-2008003746 A1 | 1/2008 |
| WO | WO-2008101975 A2 | 8/2008 |

(Continued)

OTHER PUBLICATIONS

Alho et. al., Bioorganic and Medicinal Chemistry, 2004, Elsevier, vol. 12, pp. 4431-4437.*

(Continued)

*Primary Examiner* — Sarah Pihonak
(74) *Attorney, Agent, or Firm* — Marshall, Gerstein & Borun LLP

(57) ABSTRACT

Provided are an endoparasite control agent comprising a carboxamide derivative represented by the general formula (I):

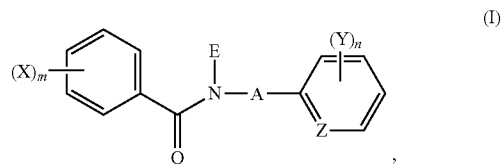

or
a salt thereof as an active ingredient, and a method for controlling endoparasites, comprising orally or parenterally administering the endoparasite control agent.

8 Claims, No Drawings

(56) References Cited

FOREIGN PATENT DOCUMENTS

| | | |
|---|---|---|
| WO | WO-2008101976 A1 | 8/2008 |
| WO | WO-2008/126922 A1 | 10/2008 |
| WO | WO-2009012998 A1 | 1/2009 |
| WO | WO-2009/127718 A2 | 10/2009 |
| WO | WO-2010/106071 A1 | 9/2010 |
| WO | WO-2010108616 A1 | 9/2010 |
| WO | WO-2013076231 A1 | 5/2013 |

OTHER PUBLICATIONS

Ducray et. al., Bioorganic and Medicinal Chemistry Letters, 2008, Elsevier, vol. 18, pp. 2935-2938.*

Written Opinion in corresponding PCT/JP2012/055190 dated Jun. 5, 2012.

International Search Report in corresponding PCT/JP2012/055190 dated Jun. 5, 2012.

Avenot et al, "Progress in understanding molecular mechanisms and evolution of resistance to succinate dehydrogenase inhibiting (SDHI) fungicides in phytopathogenic fungi," Crop Protection, vol. 29, pp. 643-651 (2010).

Infection, Inflammation & Immunity, vol. 40, pp. 310-319 (Partial Translation), 2010.

Saishin Soyaku Kagaku, The Practice of Medicinal Chemistry, vol. 1, 1st Edition, 3rd Print, Technomics, Inc., pp. 243-244 (2001). (Partial Translation).

International Preliminary Report on Patentability in corresponding PCT/JP2012/055190 dated Sep. 3, 2013.

Osanai et al., Crystallization of mitochondrial rhodoquinol-fumarate reductase from the parasitic nematode Ascaris suum with the specific inhibitor flutolanil, Acta Cryst., F65, pp. 941-944 (2009).

Extended European Search Report in corresponding PCT/JP2012/055190 dated Oct. 28, 2014.

New Zealand Examination Report for Patent Application No. 613343, dated Jul. 14, 2015.

Decision on Grant in Russian Application No. 2013144215 dated Jun. 6, 2016.

* cited by examiner

ENDOPARASITE CONTROL AGENT

TECHNICAL FIELD

The present invention relates an endoparasite control agent comprising a carboxamide derivative or a salt thereof as an active ingredient, and a method for controlling endoparasites, comprising orally or parenterally administering the endoparasite control agent.

BACKGROUND ART

Certain kinds of carboxamide derivatives have been known to have microbicidal activity (see Patent Literature 1 to 12). However, there is no description indicating that these compounds described in the literature are effective against endoparasites in animals such as mammals and birds. Further, it is known that certain kinds of carboxamide derivative are effective against nematodes that may damage agricultural products (see Patent Literature 4 or 5), but there is no specific disclosure on any effect against endoparasites in animals. Furthermore, it has been reported that compounds that inhibit succinate-ubiquinone reductase (mitochondrial complex II), which is one of the respiratory enzymes of endoparasites, can serve as an endoparasite control agent (see Non Patent Literature 1).

CITATION LIST

Patent Literature

Patent Literature 1: JP-A 01-151546
Patent Literature 2: WO 2007/060162
Patent Literature 3: JP-A 53-9739
Patent Literature 4: WO 2007/108483
Patent Literature 5: WO 2008/126922
Patent Literature 6: WO 2008/101975
Patent Literature 7: WO 2008/101976
Patent Literature 8: WO 2008/003745
Patent Literature 9: WO 2008/003746
Patent Literature 10: WO 2009/012998
Patent Literature 11: WO 2009/127718
Patent Literature 12: WO 2010/106071

Non Patent Literature

Non Patent Literature 1:
Kiyoshi Kita, "Kansen (Infection)", Winter 2010, Vol. 40-4, 310-319

SUMMARY OF INVENTION

Technical Problem

Generally, parasitosis is caused by parasites that have infected and resided in host animals, and examples of the parasites include unicellular protists (protozoa), multicellular helminths and arthropods. It is reported that the incidence of parasitosis in Japan has been remarkably decreased by improvement of environmental hygiene, but on a global scale, particularly in developing countries, parasitosis still widely prevails and causes tremendous damage. In recent years, there has been an increasing trend in the incidence of parasitic infection due to introduction of infection sources via long- or short-term overseas travelers, ingestion of food imports, ingestion of raw meat and fish meat that are more available thanks to the advance in freezing and logistics technologies, etc., and also in the incidence of parasitosis from pets etc. Another problem is that immunodeficiency caused by mass administration of immunosuppressants, anti-cancer drugs, etc. or by AIDS etc. allows usually non-pathogenic or low-pathogenic parasites to express their pathogenicity and to cause opportunistic infection in hosts. Further, parasitosis in domestic animals, such as pigs, horses, cattle, sheep, dogs, cats and domestic fowls, is a universal and serious economic problem. That is, parasitic infection of domestic animals causes anemia, malnutrition, debility, weight loss, and serious damage of intestinal tract walls, tissues and organs, and may result in decline in feed efficiency and productivity, leading to a great economic loss. Therefore, novel endoparasite control agents as a parasiticide, an antiprotozoal or the like have always been desired.

Solution to Problem

The present inventors conducted extensive research to solve the above-described problems. As a result, the present inventors found that a carboxamide derivative represented by the general formula (I) of the present invention, and a salt thereof have a high control effect against endoparasites, and then completed the present invention. That is, the present invention relates to the following.

[1] An endoparasite control agent comprising a carboxamide derivative represented by the general formula (I):

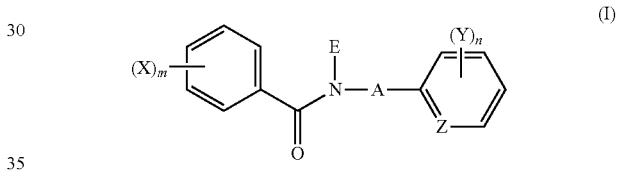

{wherein A represents a $(C_1-C_8)$ alkylene group optionally substituted by a halogen atom, a $(C_1-C_6)$ alkyl group and/or a $(C_3-C_6)$ cycloalkyl group; a $(C_1-C_8)$ alkylene group which is optionally substituted by a halogen atom, a $(C_1-C_6)$ alkyl group and/or a $(C_3-C_6)$ cycloalkyl group and is modified by incorporation, into the carbon chain, of at least one heteroatom selected from an oxygen atom, a sulfur atom, —SO—, —SO$_2$— and —N(R)— (wherein R represents a hydrogen atom, a $(C_1-C_6)$ alkyl group, a $(C_3-C_6)$ cycloalkyl group, a $(C_1-C_6)$ alkylcarbonyl group or a $(C_1-C_6)$ alkoxycarbonyl group); a $(C_2-C_8)$ alkenylene group optionally substituted by a halogen atom, a $(C_1-C_6)$ alkyl group and/or a $(C_3-C_6)$ cycloalkyl group; a $(C_2-C_8)$ alkenylene group which is optionally substituted by a halogen atom, a $(C_1-C_6)$ alkyl group and/or a $(C_3-C_6)$ cycloalkyl group and is modified by incorporation, into the carbon chain, of at least one heteroatom selected from an oxygen atom, a sulfur atom, —SO—, —SO$_2$— and —N(R)— (wherein R is as defined above); a $(C_2-C_8)$ alkynylene group optionally substituted by a halogen atom, a $(C_1-C_6)$ alkyl group and/or a $(C_3-C_6)$ cycloalkyl group; or a $(C_2-C_8)$ alkynylene group which is optionally substituted by a halogen atom, a $(C_1-C_6)$ alkyl group and/or a $(C_3-C_6)$ cycloalkyl group and is modified by incorporation, into the carbon chain, of at least one heteroatom selected from an oxygen atom, a sulfur atom, —SO—, —SO$_2$— and —N(R)— (wherein R is as defined above), and in each case, A may form a cyclic structure, where possible, E represents a hydrogen atom; a $(C_1-C_6)$ alkyl group; a $(C_3-C_6)$ cycloalkyl group; a $(C_1-C_6)$ alkoxy $(C_1-C_6)$ alkyl group; a $(C_1-C_6)$ alkylcarbonyl group; or a $(C_1-C_6)$ alkoxycarbonyl group, each X may be the same or different, and represents a halogen atom; a cyano group; a nitro group; a ($C_1$-$C_6$) alkyl group optionally substituted by a halogen atom; a ($C_1$-$C_6$) alkoxy group optionally substituted by a halogen atom; a ($C_1$-$C_6$) alkylthio group optionally substituted by a halogen atom; a ($C_1$-$C_6$) alkylsulfinyl group optionally substituted by a halogen atom; or a ($C_1$-$C_6$) alkylsulfonyl group optionally substituted by a halogen atom, m represents an integer of 0 to 5, each Y may be the same or different, and represents a halogen atom; a cyano group; a nitro group; a hydroxy group; a ($C_1$-$C_6$) alkyl group optionally substituted by a halogen atom; a ($C_2$-$C_6$) alkenyl group optionally substituted by a halogen atom; a ($C_2$-$C_6$) alkynyl group optionally substituted by a halogen atom; a ($C_1$-$C_6$) alkoxy group optionally substituted by a halogen atom; a ($C_1$-$C_6$) alkoxy ($C_1$-$C_6$) alkoxy group; a ($C_2$-$C_6$) alkenyloxy group optionally substituted by a halogen atom; a ($C_2$-$C_6$) alkynyloxy group optionally substituted by a halogen atom; a ($C_1$-$C_6$) alkylthio group optionally substituted by a halogen atom; a ($C_1$-$C_6$) alkylsulfinyl group optionally substituted by a halogen atom; a ($C_1$-$C_6$) alkylsulfonyl group optionally substituted by a halogen atom; a ($C_1$-$C_6$) alkoxycarbonyl group; a ($C_1$-$C_6$) alkoxyimino ($C_1$-$C_3$) alkyl group; a ($C_3$-$C_{30}$) trialkylsilyl group; a mono ($C_1$-$C_6$) alkylsulfonylamino group optionally substituted by a halogen atom; a phenyl group optionally substituted by one or more substituents selected from group B substituents; a phenoxy group optionally substituted by one or more substituents selected from group B substituents; a heterocyclic group optionally substituted by one or more substituents selected from group B substituents; or a heterocycloxy group optionally substituted by one or more substituents selected from group B substituents, the group B substituents are a halogen atom; a cyano group; a nitro group; a ($C_1$-$C_6$) alkyl group optionally substituted by a halogen atom; a ($C_2$-$C_6$) alkenyl group optionally substituted by a halogen atom; a ($C_2$-$C_6$) alkynyl group optionally substituted by a halogen atom; a ($C_1$-$C_6$) alkoxy group optionally substituted by a halogen atom; a ($C_2$-$C_6$) alkenyloxy group optionally substituted by a halogen atom; a ($C_2$-$C_6$) alkynyloxy group optionally substituted by a halogen atom; a ($C_1$-$C_6$) alkylthio group optionally substituted by a halogen atom; a ($C_1$-$C_6$) alkylsulfinyl group optionally substituted by a halogen atom; a ($C_1$-$C_6$) alkylsulfonyl group optionally substituted by a halogen atom; a ($C_1$-$C_6$) alkoxycarbonyl group; and a ($C_1$-$C_6$) alkoxyimino ($C_1$-$C_3$) alkyl group, n represents an integer of 0 to 5, with the proviso that when n is an integer of 2 to 5, two adjacent Y groups may join together to form a ($C_3$-$C_5$) alkylene group; a ($C_3$-$C_5$) alkenylene group; a ($C_2$-$C_4$) alkyleneoxy group; or a ($C_1$-$C_3$) alkylene dioxy group optionally substituted by a halogen atom, and Z represents a nitrogen atom; CH; or CY (wherein Y is as defined above)}, or a salt thereof as an active ingredient.

[2] The endoparasite control agent according to the above [1], wherein A represents a ($C_1$-$C_8$) alkylene group optionally substituted by a halogen atom, a ($C_1$-$C_6$) alkyl group and/or a ($C_3$-$C_6$) cycloalkyl group; or a ($C_1$-$C_8$) alkylene group which is optionally substituted by a halogen atom, a ($C_1$-$C_6$) alkyl group and/or a ($C_3$-$C_6$) cycloalkyl group and is modified by incorporation, into the carbon chain, of at least one heteroatom selected from an oxygen atom, a sulfur atom, —SO—, —$SO_2$— and —N(R)— (wherein R represents a hydrogen atom, a ($C_1$-$C_6$) alkyl group, a ($C_3$-$C_6$) cycloalkyl group, a ($C_1$-$C_6$) alkylcarbonyl group or a ($C_1$-$C_6$) alkoxycarbonyl group).

[3] The endoparasite control agent according to the above [1], wherein A represents a ($C_1$-$C_8$) alkylene group optionally substituted by a ($C_1$-$C_6$) alkyl group and/or a ($C_3$-$C_6$) cycloalkyl group; —$CR^1(R^2)$—$CR^3(R^4)$-Q- (wherein $R^1$, $R^2$, $R^3$ and $R^4$ may be the same or different from each other, and represent a hydrogen atom, a ($C_1$-$C_6$) alkyl group or a ($C_3$-$C_6$) cycloalkyl group, or $R^1$, $R^2$, $R^3$ and $R^4$ may join together in any combination to form a ($C_3$-$C_6$) cycloalkane, and Q represents an oxygen atom, a sulfur atom, —SO—, —$SO_2$— or —N(R)— (wherein R represents a hydrogen atom, a ($C_1$-$C_6$) alkyl group, a ($C_3$-$C_6$) cycloalkyl group, a ($C_1$-$C_6$) alkylcarbonyl group or a ($C_1$-$C_6$) alkoxycarbonyl group)); or —$CR^1(R^2)$—$CR^3(R^4)$—$CR^5(R^6)$-Q- (wherein $R^1$, $R^2$, $R^3$, $R^4$ and Q are as defined above, and $R^5$ and $R^6$ may be the same or different from each other, and represent a hydrogen atom, a ($C_1$-$C_6$) alkyl group or a ($C_3$-$C_6$) cycloalkyl group, or $R^1$, $R^2$, $R^3$, $R^4$, $R^5$ and $R^6$ may join together in any combination to form a ($C_3$-$C_6$) cycloalkane).

[4] The endoparasite control agent according to the above [1], wherein A represents a ($C_1$-$C_8$) alkylene group optionally substituted by a ($C_1$-$C_6$) alkyl group and/or a ($C_3$-$C_6$) cycloalkyl group; —$CR^1(R^2)$—$CR^3$ $(R^4)$-Q- (wherein $R^1$, $R^2$, $R^3$ and $R^4$ may be the same or different from each other, and represent a hydrogen atom, a ($C_1$-$C_6$) alkyl group or a ($C_3$-$C_6$) cycloalkyl group, or $R^1$, $R^2$, $R^3$ and $R^4$ may join together in any combination to form a ($C_3$-$C_6$) cycloalkane, and Q represents an oxygen atom, a sulfur atom, —SO—, —$SO_2$— or —N(R)— (wherein R represents a hydrogen atom, a ($C_1$-$C_6$) alkyl group, a ($C_3$-$C_6$) cycloalkyl group, a ($C_1$-$C_6$) alkylcarbonyl group or a ($C_1$-$C_6$) alkoxycarbonyl group)); or —$CR^4$ $(R^2)$—$CR^3$ $(R^4)$—$CR^5(R^6)$-Q- (wherein $R^1$, $R^2$, $R^3$, $R^4$ and Q are as defined above, and $R^5$ and $R^6$ may be the same or different from each other, and represent a hydrogen atom, a ($C_1$-$C_6$) alkyl group or a ($C_3$-$C_6$) cycloalkyl group, or $R^1$, $R^2$, $R^3$, $R^4$, $R^5$ and $R^6$ may join together in any combination to form a ($C_3$-$C_6$) cycloalkane), E represents a hydrogen atom; a ($C_1$-$C_6$) alkyl group; a ($C_1$-$C_6$) alkylcarbonyl group; or a ($C_1$-$C_6$) alkoxycarbonyl group, each X may be the same or different, and represents a halogen atom; a ($C_1$-$C_6$) alkyl group optionally substituted by a halogen atom; a ($C_1$-$C_6$) alkoxy group optionally substituted by a halogen atom; or a ($C_1$-$C_6$) alkylthio group optionally substituted by a halogen atom, m represents 1 or 2, each Y may be the same or different, and represents a halogen atom; a hydroxy group; a ($C_1$-$C_6$) alkyl group optionally substituted by a halogen atom; a ($C_1$-$C_6$) alkoxy group optionally substituted by a halogen atom; a ($C_1$-$C_6$) alkoxy ($C_1$-$C_6$) alkoxy group; a ($C_2$-$C_6$) alkenyloxy group optionally substituted by a halogen atom; a mono ($C_1$-$C_6$) alkylsulfonylamino group optionally substituted by a halogen atom; a phenyl group optionally substituted by one or more substituents selected from a halogen atom, a cyano group, a nitro group, a ($C_1$-$C_6$) alkyl group optionally substituted by a halogen atom, and a ($C_1$-$C_6$) alkoxy group optionally substituted by a halogen atom; a phenoxy group optionally substituted by one or more substituents selected from a halogen atom, a cyano group, a nitro group, a ($C_1$-$C_6$) alkyl group optionally substituted by a halogen atom, and a ($C_1$-$C_6$) alkoxy group optionally substituted by a halogen atom; a heterocyclic group optionally substituted by one or more substituents selected from a halogen atom, a cyano group, a nitro group, a $(C_1\text{-}C_6)$ alkyl group optionally substituted by a halogen atom, and a $(C_1\text{-}C_6)$ alkoxy group optionally substituted by a halogen atom; or a heterocycloxy group optionally substituted by one or more substituents selected from a halogen atom, a cyano group, a nitro group, a $(C_1\text{-}C_6)$ alkyl group optionally substituted by a halogen atom, and a $(C_1\text{-}C_6)$ alkoxy group optionally substituted by a halogen atom, n represents an integer of 0 to 3, with the proviso that when n is 2 or 3, two adjacent Y groups may join together to form a $(C_2\text{-}C_4)$ alkyleneoxy group or a $(C_1\text{-}C_3)$ alkylene dioxy group optionally substituted by a halogen atom, and Z represents a nitrogen atom; CH; or CY (wherein Y is as defined above).

[5] The endoparasite control agent according to the above [1], wherein A represents a $(C_1\text{-}C_5)$ alkylene group optionally substituted by a $(C_1\text{-}C_6)$ alkyl group and/or a $(C_3\text{-}C_6)$ cycloalkyl group; —$CR^1(R^2)$—$CR^3(R^4)$-Q- (wherein $R^1$, $R^2$, $R^3$ and $R^4$ may be the same or different from each other, and represent a hydrogen atom, a $(C_1\text{-}C_6)$ alkyl group or a $(C_3\text{-}C_6)$ cycloalkyl group, and Q represents an oxygen atom or a sulfur atom); or —$CR^1(R^2)$—$CR^3(R^4)$—$CR^5(R^6)$-Q- (wherein $R^1$, $R^2$, $R^3$, $R^4$ and Q are as defined above, and $R^5$ and $R^6$ may be the same or different from each other, and represent a hydrogen atom, a $(C_1\text{-}C_6)$ alkyl group or a $(C_3\text{-}C_6)$ cycloalkyl group), E represents a hydrogen atom, each X may be the same or different, and represents a halogen atom or a $(C_1\text{-}C_6)$ alkyl group optionally substituted by a halogen atom, m represents 1, each Y may be the same or different, and represents a halogen atom or a $(C_1\text{-}C_6)$ alkyl group optionally substituted by a halogen atom, n represents an integer of 1 to 3, and Z represents a nitrogen atom; CH; or CY (wherein Y is as defined above).

[6] A method for controlling endoparasites, comprising orally or parenterally administering an effective amount of the endoparasite control agent according to any one of the above [1] to [5] to a non-human mammal or a bird.

[7] A method for controlling endoparasites, comprising orally or parenterally administering an effective amount of the endoparasite control agent according to any one of the above [1] to [5] to a non-human mammal.

[8] The method according to the above [7], wherein the non-human mammal is a domestic animal.

Advantageous Effects of Invention

The present invention provides a compound useful as an endoparasite control agent which excels in performance as compared with the conventional art.

DESCRIPTION OF EMBODIMENTS

The definitions in the general formula (I) representing the carboxamide derivative of the present invention are described below.

The "$(C_1\text{-}C_8)$ alkylene group" refers to a straight $C_1\text{-}C_8$ alkylene group, for example, a methylene group, an ethylene group, a trimethylene group, a tetramethylene group, a pentamethylene group, a hexamethylene group, a heptamethylene group, an octamethylene group or the like. In the "$(C_1\text{-}C_8)$ alkylene group optionally substituted by a halogen atom, a $(C_1\text{-}C_6)$ alkyl group or a $(C_3\text{-}C_6)$ cycloalkyl group," each substituent may be bound to any carbon atom in the alkylene group. The "$(C_1\text{-}C_8)$ alkylene group which is optionally substituted by a halogen atom, a $(C_1\text{-}C_6)$ alkyl group or a $(C_3\text{-}C_6)$ cycloalkyl group and is modified by incorporation, into the carbon chain, of at least one heteroatom selected from an oxygen atom, a sulfur atom, —SO—, —$SO_2$— and —N(R)—" refers to a group which is the same as the above-mentioned optionally substituted straight $(C_1\text{-}C_8)$ alkylene group except for having such a heteroatom attached to a terminal carbon atom or inserted between carbon atoms in the alkylene group. The specific examples include an ethyleneoxy group, an ethylenethio group, an ethylene sulfinyl group, an ethylene sulfonyl group, an ethylene amino group, a propyleneoxy group, a propylenethio group, a propylene sulfinyl group, a propylene sulfonyl group, a propylene amino group, —$CH_2$—$CH_2$—O—$CH_2$—, —$CH_2$—$CH_2$—S—$CH_2$— and —$CH_2$—$CH_2$—NH—$CH_2$—.

The "$(C_2\text{-}C_8)$ alkenylene group" refers to a straight $(C_2\text{-}C_8)$ alkenylene group having one or more double bonds therein, for example, a vinylene group, a propenylene group, a butenylene group, a butadienylene group, a pentenylene group, a pentadienylene group, a hexenylene group, a hexadienylene group, a heptenylene group, a heptadienylene group, an octenylene group, an octadienylene group or the like. In the "$(C_2\text{-}C_8)$ alkenylene group optionally substituted by a halogen atom, a $(C_1\text{-}C_6)$ alkyl group or a $(C_3\text{-}C_6)$ cycloalkyl group," each substituent may be bound to any carbon atom in the alkenylene group. The "$(C_2\text{-}C_8)$ alkenylene group which is optionally substituted by a halogen atom, a $(C_1\text{-}C_6)$ alkyl group or a $(C_3\text{-}C_6)$ cycloalkyl group and is modified by incorporation, into the carbon chain, of at least one heteroatom selected from an oxygen atom, a sulfur atom, —SO—, —$SO_2$— and —N(R)—" refers to a group which is the same as the above-mentioned optionally substituted straight $(C_2\text{-}C_8)$ alkenylene group except for having such a heteroatom attached to a terminal carbon atom or inserted between carbon atoms in the alkenylene group. The specific examples include a vinyleneoxy group, a vinylenethio group, a vinylene sulfinyl group, a vinylene sulfonyl group, a vinylene amino group, a propyleneoxy group, a propylenethio group, a propylene sulfinyl group, a propylene sulfonyl group, a propylene amino group, —CH=CH—$CH_2$O—$CH_2$—, —CH=CH—$CH_2$—S—$CH_2$— and —CH=CH—$CH_2$—NH—$CH_2$—.

The "$(C_2\text{-}C_8)$ alkynylene group" refers to a straight $C_2\text{-}C_8$ alkynylene group having one or more triple bonds therein, for example, an ethynylene group, a propynylene group, a butynylene group, a butadiynylene group, a pentynylene group, a pentadiynylene group, a hexynylene group, a hexadiynylene group, a heptynylene group, a heptadiynylene group, an octynylene group, an octadiynylene group or the like. In the "$(C_2\text{-}C_8)$ alkynylene group optionally substituted by a halogen atom, a $(C_1\text{-}C_6)$ alkyl group or a $(C_3\text{-}C_6)$ cycloalkyl group," each substituent may be bound to any carbon atom in the alkynylene group. The "$(C_2\text{-}C_8)$ alkynylene group which is optionally substituted by a halogen atom, a $(C_1\text{-}C_6)$ alkyl group or a $(C_3\text{-}C_6)$ cycloalkyl group and is modified by incorporation, into the carbon chain, of at least one heteroatom selected from an oxygen atom, a sulfur atom, —SO—, —$SO_2$— and —N(R)—" refers to a group which is the same as the above-mentioned optionally substituted straight $(C_2\text{-}C_8)$ alkynylene group except for having such a heteroatom attached to a terminal carbon atom or inserted between carbon atoms in the alkynylene group. The specific examples include an ethynyleneoxy group, an ethynylenethio group, an ethynylene sulfinyl group, an ethynylene sulfonyl group, an ethynylene amino group, a propynyleneoxy group, a propynylenethio group, a propynylene sulfinyl group, a propynylene sulfonyl group, a propynylene amino group, —C≡C—CH$_2$—O—CH$_2$—, —C≡C—CH$_2$—S—CH$_2$— and —C≡C—CH$_2$—NH—CH$_2$—.

The "halogen atom" refers to a chlorine atom, a bromine atom, an iodine atom or a fluorine atom. The "(C$_1$-C$_6$) alkyl group" refers to a straight or branched alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, a neopentyl group, a n-hexyl group or the like.

The "(C$_1$-C$_6$) alkyl group optionally substituted by a halogen atom" refers to a straight or branched alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, a neopentyl group, a n-hexyl group or the like; and also refers to a straight or branched alkyl group of 1 to 6 carbon atoms substituted by one or more halogen atoms which may be the same or different from each other, for example, a trifluoromethyl group, a difluoromethyl group, a perfluoroethyl group, a hexafluoroisopropyl group, a perfluoroisopropyl group, a chloromethyl group, a bromomethyl group, a 1-bromoethyl group, a 2,3-dibromopropyl group or the like.

The "(C$_2$-C$_6$) alkenyl group optionally substituted by a halogen atom" refers to a straight or branched alkenyl group of 2 to 6 carbon atoms, for example, a vinyl group, a propenyl group, a butenyl group or the like; and also refers to a straight or branched alkenyl group of 2 to 6 carbon atoms substituted by one or more halogen atoms which may be the same or different from each other, for example, a fluorovinyl group, a difluorovinyl group, a perfluorovinyl group, a 3,3-dichloro-2-propenyl group, a 4,4-difluoro-3-butenyl group or the like.

The "(C$_2$-C$_6$) alkynyl group optionally substituted by a halogen atom" refers to a straight or branched alkynyl group of 2 to 6 carbon atoms, for example, an ethynyl group, a propynyl group, a butynyl group or the like; and also refers to a straight or branched alkynyl group of 2 to 6 carbon atoms substituted by one or more halogen atoms which may be the same or different from each other, for example, a fluoroethynyl group, a perfluoropropynyl group, a 4,4,4-trifluoro-2-butynyl group or the like.

The "(C$_1$-C$_6$) alkoxy group optionally substituted by a halogen atom" refers to a straight or branched alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a neopentyloxy group, a n-hexyloxy group or the like; and also refers to a straight or branched alkoxy group of 1 to 6 carbon atoms substituted by one or more halogen atoms which may be the same or different from each other, for example, a trifluoromethoxy group, a difluoromethoxy group, a perfluoroethoxy group, a perfluoroisopropoxy group, a chloromethoxy group, a bromomethoxy group, a 1-bromoethoxy group, a 2,3-dibromopropoxy group or the like.

The "(C$_1$-C$_6$) alkoxy (C$_1$-C$_6$) alkoxy group" refers to a straight or branched alkoxy group of 1 to 6 carbon atoms having a straight or branched alkoxy group of 1 to 6 carbon atoms as a substituent at a substitutable position, for example, a methoxymethoxy group, an ethoxymethoxy group, a 1-methoxyethoxy group, a 2-methoxyethoxy group, a 1-ethoxyethoxy group, a 2-ethoxyethoxy group or the like.

The "(C$_1$-C$_6$) alkoxy (C$_1$-C$_6$) alkyl group" refers to a straight or branched alkyl group of 1 to 6 carbon atoms having a straight or branched alkoxy group of 1 to 6 carbon atoms as a substituent at a substitutable position, for example, a methoxymethyl group, an ethoxymethyl group, a 1-methoxyethyl group, a 2-methoxyethyl group, a 1-ethoxyethyl group, a 2-ethoxyethyl group or the like.

The "(C$_2$-C$_6$) alkenyloxy group optionally substituted by a halogen atom" refers to a straight or branched alkenyloxy group of 2 to 6 carbon atoms, for example, a propenyloxy group, a butenyloxy group, a pentenyloxy group or the like; and also refers to a straight or branched alkenyloxy group of 2 to 6 carbon atoms substituted by one or more halogen atoms which may be the same or different from each other, for example, a fluorovinyloxy group, a difluorovinyloxy group, a perfluorovinyloxy group, a 3,3-dichloro-2-propenyloxy group, a 4,4-difluoro-3-butenyloxy group or the like.

The "(C$_2$-C$_6$) alkynyloxy group optionally substituted by a halogen atom" refers to a straight or branched alkynyloxy group of 2 to 6 carbon atoms, for example, a propynyloxy group, a butynyloxy group, a pentynyloxy group or the like; and also refers to a straight or branched alkynyloxy group of 2 to 6 carbon atoms substituted by one or more halogen atoms which may be the same or different from each other, for example, a fluoroethynyloxy group, a perfluoropropynyloxy group, a 4,4,4-trifluoro-2-butynyloxy group or the like.

The "(C$_1$-C$_6$) alkylthio group optionally substituted by a halogen atom" refers to a straight or branched alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a n-hexylthio group or the like; and also refers to a straight or branched alkylthio group of 1 to 6 carbon atoms substituted by one or more halogen atoms which may be the same or different from each other, for example, a trifluoromethylthio group, a difluoromethylthio group, a perfluoroethylthio group, a perfluoroisopropylthio group, a chloromethylthio group, a bromomethylthio group, a 1-bromoethylthio group, a 2,3-dibromopropylthio group or the like.

The "(C$_1$-C$_6$) alkylsulfinyl group optionally substituted by a halogen atom" refers to a straight or branched alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a n-hexylsulfinyl group or the like; and also refers to a straight or branched alkylsulfinyl group of 1 to 6 carbon atoms substituted by one or more halogen atoms which may be the same or different from each other, for example, a trifluoromethylsulfinyl group, a difluoromethylsulfinyl group, a perfluoroethylsulfinyl group, a perfluoroisopropylsulfinyl group, a chloromethylsulfinyl group, a bromomethylsulfinyl group, a 1-bromoethylsulfinyl group, a 2,3-dibromopropylsulfinyl group or the like.

The "(C$_1$-C$_6$) alkylsulfonyl group optionally substituted by a halogen atom" refers to a straight or branched alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a n-hexylsulfonyl group or the like; and also refers to a straight or branched alkylsulfonyl group of 1 to 6 carbon atoms substituted by one or more halogen atoms which may be the same or different from each other, for example, a trifluoromethylsulfonyl group, a difluoromethylsulfonyl group, a perfluoroethylsulfonyl group, a perfluoroisopropylsulfonyl group, a chloromethylsulfonyl group, a bromomethylsulfonyl group, a 1-bromoethylsulfonyl group, a 2,3-dibromopropylsulfonyl group or the like.

The "$(C_1-C_6)$ alkylcarbonyl group" refers to a straight or branched alkyl group of 1 to 6 carbon atoms bound to a carbonyl group, for example, a methylcarbonyl group, an ethylcarbonyl group, a n-propylcarbonyl group, an isopropylcarbonyl group, a n-butylcarbonyl group, a tert-butylcarbonyl group or the like.

The "$(C_1-C_6)$ alkoxycarbonyl group" refers to a straight or branched alkoxy group of 1 to 6 carbon atoms bound to a carbonyl group, for example, a methoxycarbonyl group, an ethoxycarbonyl group, a n-propoxycarbonyl group, an iso-propoxycarbonyl group, a n-butoxycarbonyl group, a tert-butoxycarbonyl group or the like.

The "$(C_1-C_6)$ alkoxyimino $(C_1-C_3)$ alkyl group" refers to a straight or branched alkoxy group of 1 to 6 carbon atoms bound to an imino $(C_1-C_3)$ alkyl group, for example, a methoxyimino methyl group, an ethoxyimino methyl group, a n-propoxyimino methyl group, an isopropoxyimino ethyl group or the like.

The "$(C_3-C_{30})$ trialkylsilyl group" refers to a straight or branched alkylsilyl group of 3 to 30 carbon atoms in total, for example, a trimethylsilyl group, a triethylsilyl group or the like.

The "mono$(C_1-C_6)$ alkylsulfonylamino group optionally substituted by a halogen atom" refers to a straight or branched monoalkylsulfonylamino group of 1 to 6 carbon atoms, for example, a methylsulfonylamino group, an ethylsulfonylamino group, an isopropylsulfonylamino group or the like; and also refers to a straight or branched monoalkylsulfonylamino group of 1 to 6 carbon atoms substituted by one or more halogen atoms which may be the same or different from each other, for example, a trifluoromethylsulfonylamino group or the like.

The "$(C_3-C_6)$ cycloalkane" that $R^1$, $R^2$, $R^3$ and $R^4$ may join together in any combination to form and the "$(C_3-C_6)$ cycloalkane" that $R^1$, $R^2$, $R^3$, $R^4$, $R^5$ and $R^6$ may join together in any combination to form are, for example, cyclopropane, cyclobutane, cyclopentane, cyclohexane or the like.

Examples of the "$(C_2-C_4)$ alkyleneoxy group" include —CH$_2$—CH$_2$—O—, CH$_2$—C(CH$_3$)$_2$—O—, —CH$_2$—CH$_2$—CH$_2$—O— and —CH$_2$—CH$_2$—CH$_2$—CH$_2$—O—.

The "$(C_1-C_3)$ alkylene dioxy group optionally substituted by a halogen atom" refers to an alkylene dioxy group of 1 to 3 carbon atoms, for example, —O—CH$_2$—O—, —O—CH$_2$—CH$_2$—O—, —O—CH$_2$—CH$_2$—CH$_2$—O— or the like; and also refers to an alkylene dioxy group of 1 to 3 carbon atoms substituted by one or more halogen atoms which may be the same or different from each other, for example, —O—CF$_2$—O—, —O—CF$_2$—CF$_2$—O—, —O—CCl$_2$—O— or the like.

The "heterocyclic group" refers to a 5- or 6-membered monocyclic aromatic or 3- or 6-membered monocyclic non-aromatic heterocyclic group containing, as ring atoms, a carbon atom(s) and 1 to 4 heteroatoms selected from an oxygen atom, a sulfur atom and a nitrogen atom; and also refers to a condensed heterocyclic group formed by condensation of such a monocyclic aromatic or non-aromatic heterocycle with a benzene ring or by condensation of such monocyclic aromatic or non-aromatic heterocycles (the heterocycles may be different from each other).

Examples of the "aromatic heterocyclic group" include monocyclic aromatic heterocyclic groups, such as furyl, thienyl, pyridyl, pyrimidinyl, pyridazinyl, pyrazinyl, pyrrolyl, imidazolyl, pyrazolyl, thiazolyl, isothiazolyl, oxazolyl, isoxazolyl, oxadiazolyl, thiadiazolyl, triazolyl, tetrazolyl and triazinyl; and aromatic condensed heterocyclic groups, such as quinolyl, isoquinolyl, quinazolyl, quinoxalyl, benzofuranyl, benzothienyl, benzoxazolyl, benzisoxazolyl, benzothiazolyl, benzimidazolyl, benzotriazolyl, indolyl, indazolyl, pyrrolopyrazinyl, imidazopyridinyl, imidazopyrazinyl, pyrazolopyridinyl, pyrazolothienyl and pyrazolotriazinyl.

Examples of the "non-aromatic heterocyclic group" include monocyclic non-aromatic heterocyclic groups, such as oxiranyl, thiiranyl, aziridinyl, oxetanyl, thietanyl, azetidinyl, pyrrolidinyl, piperidinyl, morpholinyl, thiomorpholinyl, piperazinyl, hexamethyleneiminyl, oxazolidinyl, thiazolidinyl, imidazolidinyl, oxazolinyl, thiazolinyl, imidazolinyl, dioxolyl, dioxolanyl, dihydrooxadiazolyl, 2-oxo-1,3-oxazolidin-5-yl, pyranyl, tetrahydropyranyl, thiopyranyl, tetrahydrothiopyranyl, 1-oxide tetrahydrothiopyranyl, 1,1-dioxide tetrahydrothiopyranyl, tetrahydrofuryl, dioxanyl, pyrazolidinyl, pyrazolinyl, tetrahydropyrimidinyl, dihydrotriazolyl and tetrahydrotriazolyl; and non-aromatic condensed heterocyclic groups, such as dihydroindolyl, dihydroisoindolyl, dihydrobenzofuranyl, dihydrobenzodioxinyl, dihydrobenzodioxepinyl, tetrahydrobenzofuranyl, chromenyl, dihydroquinolinyl, tetrahydroquinolinyl, dihydroisoquinolinyl, tetrahydroisoquinolinyl and dihydrophthalazinyl.

Examples of a salt of the carboxamide derivative represented by the general formula (I) of the present invention include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

As the carboxamide derivative of the present invention, preferred is a compound of the general formula (I) wherein A represents a $(C_1-C_8)$ alkylene group optionally substituted by a $(C_1-C_6)$ alkyl group and/or a $(C_3-C_6)$ cycloalkyl group; —CR$^1$(R$^2$)—CR$^3$(R$^4$)-Q- (wherein R$^1$, R$^2$, R$^3$ and R$^4$ may be the same or different from each other, and represent a hydrogen atom, a $(C_1-C_6)$ alkyl group or a $(C_3-C_6)$ cycloalkyl group, or R$^1$, R$^2$, R$^3$ and R$^4$ may join together in any combination to form a $(C_3-C_6)$ cycloalkane, and Q represents an oxygen atom, a sulfur atom, —SO—, —SO$_2$— or —N(R)— (wherein R represents a hydrogen atom, a $(C_1-C_6)$ alkyl group, a $(C_3-C_6)$ cycloalkyl group, a $(C_1-C_6)$ alkylcarbonyl group or a $(C_1-C_6)$ alkoxycarbonyl group)); or —CR$^1$(R$^2$)—CR$^3$(R$^4$)—CR$^5$(R$^6$)-Q- (wherein R$^1$, R$^2$, R$^3$, R$^4$ and Q are as defined above, and R$^5$ and R$^6$ may be the same or different from each other, and represent a hydrogen atom, a $(C_1-C_6)$ alkyl group join together in any combination to form a $(C_3-C_6)$ cycloalkane), E represents a hydrogen atom; a $(C_1-C_6)$ alkyl group; a $(C_1-C_6)$ alkylcarbonyl group; or a $(C_1-C_6)$ alkoxycarbonyl group, each X may be the same or different, and represents a halogen atom; a $(C_1-C_6)$ alkyl group optionally substituted by a halogen atom; a $(C_1-C_6)$ alkoxy group optionally substituted by a halogen atom; or a $(C_1-C_6)$ alkylthio group optionally substituted by a halogen atom, m represents 1 or 2, each Y may be the same or different, and represents a halogen atom; a hydroxy group; a $(C_1-C_6)$ alkyl group optionally substituted by a halogen atom; a $(C_1-C_6)$ alkoxy group optionally substituted by a halogen atom; a $(C_1-C_6)$ alkoxy $(C_1-C_6)$ alkoxy group; a $(C_2-C_6)$ alkenyloxy group optionally substituted by a halogen atom; a mono $(C_1-C_6)$ alkylsulfonylamino group optionally substituted by a halogen atom; a phenyl group optionally substituted by one or more substituents selected from a halogen atom, a cyano group, a nitro group, a $(C_1-C_6)$ alkyl group optionally substituted by a halogen atom, and a $(C_1-C_6)$ alkoxy group optionally substituted by a halogen atom; a phenoxy group optionally substituted by one or more substituents selected from a halogen atom, a cyano group, a nitro group, a $(C_1-C_6)$ alkyl group optionally substituted by a halogen atom, and a $(C_1-C_6)$ alkoxy group optionally substituted by a halogen atom; a heterocyclic group optionally substituted by one or more substituents selected from a halogen atom, a cyano group, a nitro group, a $(C_1-C_6)$ alkyl group optionally substituted by a halogen atom, and a $(C_1-C_6)$ alkoxy group optionally substituted by a halogen atom; or a heterocycloxy group optionally substituted by one or more substituents selected from a halogen atom, a cyano group, a nitro group, a $(C_1-C_6)$ alkyl group optionally substituted by a halogen atom, and a $(C_1-C_6)$ alkoxy group optionally substituted by a halogen atom, n represents an integer of 0 to 3, with the proviso that when n is 2 or 3, two adjacent Y groups may join together to form a $(C_2-C_4)$ alkyleneoxy group or a $(C_1-C_3)$ alkylene dioxy group optionally substituted by a halogen atom, and Z represents a nitrogen atom; CH; or CY (wherein Y is as defined above).

More preferred is a compound of the general formula (I) wherein A represents a $(C_1-C_5)$ alkylene group optionally substituted by a $(C_1-C_6)$ alkyl group and/or a $(C_3-C_6)$ cycloalkyl group; —CR$^1$(R$^2$)—CR$^3$ (R$^4$)-Q- (wherein R$^1$, R$^2$, R$^3$ and R$^4$ may be the same or different from each other, and represent a hydrogen atom, a $(C_1-C_6)$ alkyl group or a $(C_3-C_6)$ cycloalkyl group, and Q represents an oxygen atom or a sulfur atom); or —CR$^1$(R$^2$)—CR$^3$ (R$^4$)—CR$^5$(R$^6$)-Q- (wherein R$^1$, R$^2$, R$^3$, R$^4$ and Q are as defined above, and R$^5$ and R$^6$ may be the same or different from each other, and represent a hydrogen atom, a $(C_1-C_6)$ alkyl group or a $(C_3-C_6)$ cycloalkyl group), E represents a hydrogen atom, each X may be the same or different, and represents a halogen atom or a $(C_1-C_6)$ alkyl group optionally substituted by a halogen atom, m represents 1, each Y may be the same or different, and represents a halogen atom or a $(C_1-C_6)$ alkyl group optionally substituted by a halogen atom, n represents an integer of 1 to 3, and Z represents a nitrogen atom; CH; or CY (wherein Y is as defined above).

The compound represented by the general formula (I) of the present invention is a known compound, and can be produced by the production method described in JP-A 01-151546, WO 2007/060162, JP-A 53-9739, WO 2007/108483, WO 2008/101975, WO 2008/101976, WO 2008/003745, WO 2008/003746, WO 2009/012998, WO 2009/127718 or WO 2010/106071, the method described in Shin-Jikken Kagaku Kouza 14 (Maruzen, Dec. 20, 1977), a modified method of the foregoing, or the like.

Representative examples of the carboxamide derivative represented by the general formula (I) of the present invention are shown in Table 1, but the present invention is not limited thereto. In Table 1, "Me" represents a methyl group, "Et" represents an ethyl group, "Pr" represents a propyl group, "Bu" represents a butyl group, "Ph" represents a phenyl group, "c-" represents cyclo, "i-" represents iso, "t-" represents tertiary, and the physical property refers to a melting point (° C.).

Regarding the compounds shown with the note "Paste" in the column "Physical property" in Table 1, their $^1$HNMR spectrum data are shown in Table 5. $Q_1$ to $Q_7$ represent the following structures.

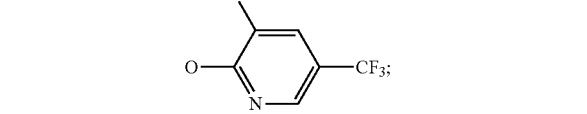

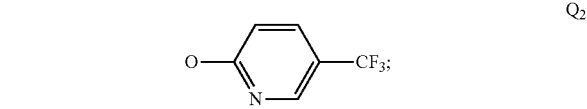

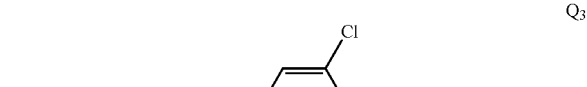

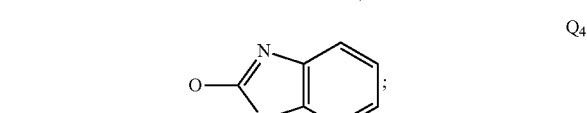

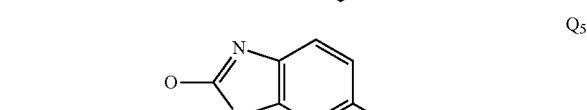

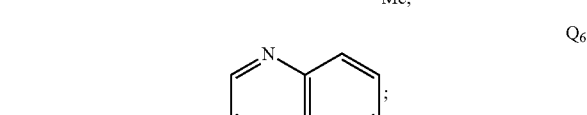

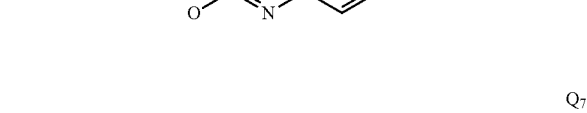

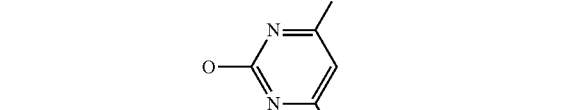

TABLE 1

| Compound No. | $(X)_m$ | $R^1$ | $R^2$ | $R^3$ | $R^4$ | $(Y)_n$ | Physical property |
|---|---|---|---|---|---|---|---|
| 1-1 | 2-CF$_3$ | H | H | H | H | 2-Cl | 104.9-105.7 |
| 1-2 | 2-CF$_3$ | H | H | H | H | 3-CF$_3$ | 63-65 |
| 1-3 | 2-CF$_3$ | H | H | H | H | 4-Cl | 116.6-117.6 |
| 1-4 | 2-CF$_3$ | H | H | Me | H | 4-Cl | 89 |
| 1-5 | 2-CF$_3$ | H | H | Me | Me | 4-Cl | 91-92 |
| 1-6 | 2-CF$_3$ | H | H | Et | H | 4-Cl | Paste |
| 1-7 | 2-CF$_3$ | H | H | Me | Et | 4-Cl | Paste |
| 1-8 | 2-CF$_3$ | H | H | Et | Et | 4-Cl | Paste |
| 1-9 | 2-CF$_3$ | H | H | i-Bu | H | 4-Cl | Paste |
| 1-10 | 2-I | H | H | Me | H | 4-Cl | 119 |
| 1-11 | 2-I | H | H | Me | Me | 4-Cl | 121-122 |
| 1-12 | 2-I | H | H | Et | H | 4-Cl | 103 |
| 1-13 | 2-I | H | H | Me | Et | 4-Cl | Paste |
| 1-14 | 2-I | H | H | Et | Et | 4-Cl | Paste |
| 1-15 | 2-I | H | H | i-Bu | H | 4-Cl | 86-91 |
| 1-16 | 2-CF$_3$ | H | H | H | H | 2,4-Cl$_2$ | 104.2-105.2 |
| 1-17 | 2-CF$_3$ | H | H | H | H | 2,3-Cl$_2$ | 135-136 |
| 1-18 | 2-I | H | H | H | H | 2,3-Cl$_2$ | 145-146 |
| 1-19 | 2-CF$_3$ | H | H | H | H | 2,6-Cl$_2$ | 148.4-149.4 |
| 1-20 | 2-CF$_3$ | H | H | H | H | 3,4-Cl$_2$ | 95-96.8 |
| 1-21 | 2-I | H | H | H | H | 3,4-Cl$_2$ | 107.2-109.2 |
| 1-22 | 2-CF$_3$ | H | H | H | H | 2-Cl-4-F | 81.5-82.8 |
| 1-23 | 2-CF$_3$ | H | H | H | H | 2-Me-4-Cl | 97-98 |
| 1-24 | 2-I | H | H | H | H | 2-Me-4-Cl | 121-122.7 |
| 1-25 | 2-CF$_3$ | H | H | H | H | 2,5-Cl$_2$ | 89.8-90.9 |
| 1-26 | 2-CF$_3$ | H | H | H | H | 2,4-(CF$_3$)$_2$ | 112.9-113.9 |
| 1-27 | 2-CF$_3$ | H | H | H | H | 2,4-Me$_2$ | 75.1-77.2 |
| 1-28 | 2-CF$_3$ | H | H | H | H | 2,5-Me$_2$ | 94-95 |
| 1-29 | 2-I | H | H | H | H | 2,5-Me$_2$ | 115-116 |
| 1-30 | 2-CF$_3$ | H | H | H | H | 2-Cl-5-CF$_3$ | 95.7-96.9 |
| 1-31 | 2-I | H | H | H | H | 2-Cl-5-CF$_3$ | 122-123 |
| 1-32 | 2-CF$_3$ | Me | H | H | H | 2,4-Cl$_2$ | 142 |
| 1-33 | 2-I | Me | H | H | H | 2,4-Cl$_2$ | 161-162 |
| 1-34 | 2-CF$_3$ | H | H | CH$_2$CH$_2$ | | 2,4-Cl$_2$ | 108-112 |
| 1-35 | 2-I | H | H | CH$_2$CH$_2$ | | 2,4-Cl$_2$ | 101-103 |
| 1-36 | 2-F | H | H | CH$_2$CH$_2$ | | 2,4-Cl$_2$ | 99-101 |
| 1-37 | 2-CF$_3$ | Me | H | CH$_2$CH$_2$ | | 2,4-Cl$_2$ | 107-110 |
| 1-38 | 2-I | Me | H | CH$_2$CH$_2$ | | 2,4-Cl$_2$ | 50-51 |
| 1-39 | 2-CF$_3$ | H | H | H | H | 2-F-4-CF$_3$ | 94-97 |
| 1-40 | 2-I | H | H | H | H | 2-F-4-CF$_3$ | 118 |
| 1-41 | 2-SCHF$_2$ | H | H | H | H | 2,4-Cl$_2$ | 103 |
| 1-42 | 2-I | H | H | H | H | 2,4-Cl$_2$ | 125-126 |
| 1-43 | 2-Br | H | H | H | H | 2,4-Cl$_2$ | 127-128 |
| 1-44 | 2-Cl | H | H | H | H | 2,4-Cl$_2$ | 124-126 |
| 1-45 | 2-Me | H | H | H | H | 2,4-Cl$_2$ | 136-138 |
| 1-46 | 2-F | H | H | H | H | 2,4-Cl$_2$ | 78 |
| 1-47 | 2,6-F$_2$ | H | H | H | H | 2,4-Cl$_2$ | 75-76 |
| 1-48 | 2-OCF$_3$ | H | H | H | H | 2,4-Cl$_2$ | 88-90 |
| 1-49 | 2-CF$_3$ | H | H | H | H | 4-Ph(4'-OCF$_3$) | 64-65 |
| 1-50 | 2-CF$_3$ | H | H | H | H | 2-F-4-Ph(4'-OCF$_3$) | 146-148 |
| 1-51 | 2-CF$_3$ | H | H | H | H | 2-Cl-4-CF$_3$ | 102-103 |
| 1-52 | 2-CF$_3$ | H | H | H | H | 2-F-4-Cl | 101-102 |
| 1-53 | 2-CF$_3$ | H | H | H | H | 2-Me-4-CF(CF$_3$)$_2$ | Paste |
| 1-54 | 2-I | H | H | H | H | 2-Me-4-CF(CF$_3$)$_2$ | 98-100 |
| 1-55 | 2-CF$_3$ | H | H | H | H | 2,4-F$_2$ | 94.4-95.8 |
| 1-56 | 2-CF$_3$ | H | H | H | H | 2-Cl-4-OCHF$_2$ | |
| 1-57 | 2-CF$_3$ | H | H | H | H | 2-Cl-4-Q$_1$ | 135.7-137.2 |
| 1-58 | 2-CF$_3$ | H | H | H | H | 2-Cl-4-Q$_2$ | 137.8-138.8 |
| 1-59 | 2-CF$_3$ | H | H | H | H | 2-Cl-4-OPh | Paste |
| 1-60 | 2-CF$_3$ | H | H | H | H | 2-Cl-4-OPh(4'-CF$_3$) | 109.6-111.5 |
| 1-61 | 2-CF$_3$ | H | H | H | H | 2,4,5-Cl$_3$ | 130-131.6 |
| 1-62 | 2-CF$_3$ | H | H | H | H | 2,4,5-F$_3$ | |
| 1-63 | 2-CF$_3$ | Me | H | H | H | 2-Cl-4-CF$_3$ | 144.5-145.5 |
| 1-64 | 2-CF$_3$ | Me | H | H | H | 2,4-F$_2$ | 121.5-124.5 |
| 1-65 | 2-CF$_3$ | Me | H | H | H | 2-F-4-Cl | 140.7-142.3 |
| 1-66 | 2-CF$_3$ | Me | H | H | H | 2-Cl-4-OH | 169.2-171.6 |
| 1-67 | 2-CF$_3$ | Me | H | H | H | 2-Cl-4-OCHF$_2$ | |
| 1-68 | 2-CF$_3$ | Me | H | H | H | 2-Cl-4-OCH$_2$OCH$_3$ | 109.2-112.9 |
| 1-69 | 2-CF$_3$ | Me | H | H | H | 2-Cl-4-Q$_1$ | 159.5-160.8 |
| 1-70 | 2-CF$_3$ | Me | H | H | H | 2-Cl-4-Q$_2$ | |
| 1-71 | 2-CF$_3$ | Me | H | H | H | 2-Cl-4-Q$_3$ | 123.9-125.4 |
| 1-72 | 2-CF$_3$ | Me | H | H | H | 2-Cl-4-Q$_4$ | |
| 1-73 | 2-CF$_3$ | Me | H | H | H | 2-Cl-4-Q$_5$ | |
| 1-74 | 2-CF$_3$ | Me | H | H | H | 2-Cl-4-Q$_6$ | |
| 1-75 | 2-CF$_3$ | Me | H | H | H | 2-Cl-4-Q$_7$ | |
| 1-76 | 2-CF$_3$ | Me | H | H | H | 2-Cl-4-OPh | 118.3-119.8 |
| 1-77 | 2-CF$_3$ | Me | H | H | H | 2-Cl-4-OPh(4'-CF$_3$) | |

TABLE 1-continued

| Compound No. | (X)$_m$ | R$^1$ | R$^2$ | R$^3$ | R$^4$ | (Y)$_n$ | Physical property |
|---|---|---|---|---|---|---|---|
| 1-78 | 2-CF$_3$ | Me | H | H | H | 2-Cl-4-OPh(4'-Cl) | |
| 1-79 | 2-CF$_3$ | Me | H | H | H | 2,4,5-F$_3$ | 146.9-148.7 |
| 1-80 | 2-CF$_3$ | Me | H | H | H | 2,4,5-Cl$_3$ | |
| 1-81 | 2-CF$_3$ | Me | H | H | H | 3,4-Cl$_2$ | 133 |
| 1-82 | 2-I | Me | H | H | H | 3,4-Cl$_2$ | 143 |
| 1-83 | 2-CF$_3$ | Me | H | H | H | 3-OCF$_2$O-4 | |
| 1-84 | 2-CF$_3$ | Me | H | H | H | 3-OCF$_2$CF$_2$O-4 | |
| 1-85 | 2-CF$_3$ | Me | H | H | H | 2-Cl, 4-OCF$_2$O-5 | |
| 1-86 | 2-CF$_3$ | Me | H | H | H | 2-F, 4-OCF$_2$O-5 | |
| 1-87 | 2-CF$_3$ | Me | Me | H | H | 2,4-Cl$_2$ | 121 |
| 1-88 | 2-CF$_3$ | Me | Me | H | H | 3,4-Cl$_2$ | |
| 1-89 | 2-CF$_3$ | Me | Me | H | H | 2,4-F$_2$ | |
| 1-90 | 2-CF$_3$ | Me | Me | H | H | 3,4-F$_2$ | |
| 1-91 | 2-CF$_3$ | CH$_2$CH$_2$ | | H | H | 2,4-Cl$_2$ | |
| 1-92 | 2-CF$_3$ | CH$_2$CH$_2$ | | H | H | 2-Cl-4-CF$_3$ | |
| 1-93 | 2-CF$_3$ | CH$_2$CH$_2$ | | H | H | 2-F-4-CF$_3$ | |
| 1-94 | 2-CF$_3$ | H | H | H | H | 2,5-F$_2$-4-Cl | 95.4-96.2 |
| 1-95 | 2-CF$_3$ | Me | H | H | H | 2,5-F$_2$-4-Cl | |
| 1-96 | 2-CF$_3$ | H | H | H | H | 2-Cl-4,5-F$_2$ | |
| 1-97 | 2-CF$_3$ | Me | H | H | H | 2-Cl-4,5-F$_2$ | |
| 1-98 | 2-CF$_3$ | H | H | H | H | 2-F-4,5-Cl$_2$ | |
| 1-99 | 2-CF$_3$ | Me | H | H | H | 2-F-4,5-Cl$_2$ | |
| 1-100 | 2-CF$_3$ | H | H | H | H | 2,4-Cl$_2$-5-F | 98.7-99 |
| 1-101 | 2-CF$_3$ | Me | H | H | H | 2,4-Cl$_2$-5-F | |
| 1-102 | 2-CF$_3$ | H | H | H | H | 2-Cl-4-SMe | 74.1-76.3 |
| 1-103 | 2-CF$_3$ | Me | H | H | H | 2-Cl-4-SMe | 125.4-128.4 |
| 1-104 | 2-CF$_3$ | H | H | H | H | 2-Cl-4-SOMe | 128.9-129.6 |
| 1-105 | 2-CF$_3$ | H | H | H | H | 2-Cl-4-SO$_2$Me | 135.4-137.1 |
| 1-106 | 2-CF$_3$ | Me | H | H | H | 2-Br-4-Cl | 143 |
| 1-107 | 2-CF$_3$ | H | H | H | H | 2-Br-4-F | 106.4 |
| 1-108 | 2-CF$_3$ | H | H | H | H | 3-OCF$_2$O-4 | 126 |
| 1-109 | 2,6-F$_2$ | H | H | H | H | 2-Cl-4-Q$_1$ | 134.6-136.7 |
| 1-110 | 2-CF$_3$ | H | H | H | H | 2,6-Cl$_2$-4-CF$_3$ | 153.2-154.2 |
| 1-111 | 2-CF$_3$ | H | H | H | H | H | 98-99 |
| 1-112 | 2-CF$_3$ | H | H | Me | Me | 2,4-Cl$_2$ | Paste |

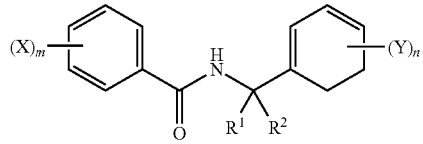

(I-2)

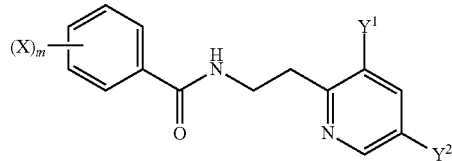

(I-3)

TABLE 2

| Compound No. | (X)$_m$ | R$^1$ | R$^2$ | (Y)$_n$ | Physical property |
|---|---|---|---|---|---|
| 2-1 | 2-CF$_3$ | H | H | 4-t-Bu | 104-105 |
| 2-2 | 2-CF$_3$ | H | H | 3-CF$_3$SO$_2$NH | 120-121 |
| 2-3 | 2-CF$_3$ | Me | Me | H | 122-124 |
| 2-4 | 2-CF$_3$ | c-Pr | H | 4-Cl | 127-130 |
| 2-5 | 2-CF$_3$ | H | H | 3-Me-4-Ph(4'-OCF$_3$) | 122-123 |
| 2-6 | 2-CF$_3$ | H | H | 2,4-Cl$_2$ | 143-144 |
| 2-7 | 2-CF$_3$ | Me | H | 2,4-Cl$_2$ | 148-149 |
| 2-8 | 2-CF$_3$ | Me | H | 4-Cl | 128-129 |
| 2-9 | 4-t-Bu | H | H | 4-t-Bu | 137-138 |
| 2-10 | 2,6-F$_2$ | H | H | 4-t-Bu | 56-58 |

TABLE 3

| Compound No. | (X)$_m$ | Y$^1$ | Y$^2$ | Physical property value |
|---|---|---|---|---|
| 3-1 | 2-Cl | Cl | CF$_3$ | 95-96 |
| 3-2 | 2-Br | Cl | CF$_3$ | 104-106 |
| 3-3 | 2-I | Cl | CF$_3$ | 128-129 |
| 3-4 | 2-CH$_3$ | Cl | CF$_3$ | 107-109 |
| 3-5 | 2-CF$_3$ | H | H | 112-113 |
| 3-6 | 2-CF$_3$ | H | CF$_3$ | 91-92 |
| 3-7 | 2-CF$_3$ | Cl | CF$_3$ | 106-111 |
| 3-8 | 2-SCH$_3$ | Cl | CF$_3$ | 89-90 |
| 3-9 | 4-CF$_3$ | Cl | CF$_3$ | 151-152 |
| 3-10 | 2,6-F | Cl | CF$_3$ | 98-99 |
| 3-11 | 2,6-Cl | Cl | CF$_3$ | 110-111 |

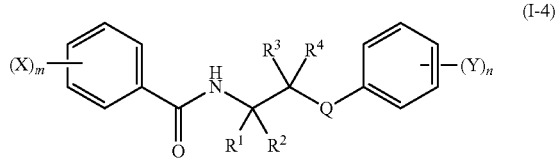

(I-4)

TABLE 4

| Compound No. | $(X)_m$ | $R^1$ | $R^2$ | $R^3$ | $R^4$ | Q | $(Y)_n$ | Physical property |
|---|---|---|---|---|---|---|---|---|
| 4-1 | 2-CF$_3$ | H | H | H | H | O | 2,4-Cl$_2$ | 95.5-96.4 |
| 4-2 | 2-CF$_3$ | Me | H | H | H | O | 2,4-Cl$_2$ | 110.8-112.4 |
| 4-3 | 2-CF$_3$ | H | H | H | H | O | 2,4-Me$_2$ | 101.5-103.9 |
| 4-4 | 2-CF$_3$ | H | H | H | H | CH$_2$O | 2,4-Cl$_2$ | 92.6-95.3 |
| 4-5 | 2-CF$_3$ | H | H | H | H | CH$_2$S | 2,4-Me$_2$ | 98.4-99.9 |
| 4-6 | 2-CF$_3$ | H | H | H | H | CH$_2$S | 2,4-Cl$_2$ | 121.6-122.2 |
| 4-7 | 2-CF$_3$ | H | H | H | H | CH$_2$ | 2,4-Cl$_2$ | 115.3-116.9 |
| 4-8 | 2-CF$_3$ | Me | H | H | H | CH$_2$ | 2,4-Cl$_2$ | 130.4-131.4 |
| 4-9 | 2-CF$_3$ | H | H | H | Me | O | 2,4-Cl$_2$ | |
| 4-10 | 2-CF$_3$ | H | H | H | H | S | 2,4-Cl$_2$ | |

TABLE 5

| Compound No. | $^1$H-NMR[CDCl$_3$/TMS, δ value (ppm)] |
|---|---|
| 1-6 | 7.65 (dd, 1H), 7.51 (m, 2H), 7.32 (dd, 1H), 7.30 (d, 2H), 7.14 (d, 2H), 5.58 (br, 1H), 3.92 (m, 1H), 3.38 (m, 1H), 2.80 (m, 1H), 1.79 (m, 1H), 1.60 (m, 1H), 0.83 (t, 3H) |
| 1-7 | 7.65 (d, 1H), 7.51 (m, 2H), 7.25-7.36 (m, 5H), 5.40 (br, 1H), 3.77 (dd, 1H), 3.59 (dd, 1H), 1.80 (m, 1H), 1.66 (m, 1H), 1.37 (s, 3H), 0.74 (t, 3H) |
| 1-8 | 7.65 (dd, 1H), 7.51 (m, 2H), 7.26-7.37 (m, 5H), 5.31 (br, 1H), 3.74 (d, 2H), 1.75 (m, 4H), 0.79 (t, 6H) |
| 1-9 | 7.65 (dd, 1H), 7.51 (m, 2H), 7.32 (dd, 1H), 7.29 (d, 2H), 7.15 (d, 2H), 5.56 (br, 1H), 3.87 (m, 1H), 3.33 (m, 1H), 2.98 (m, 1H), 1.53 (m, 2H), 1.40 (m, 1H), 0.87 (t, 6H) |
| 1-13 | 7.81 (dd, 1H), 7.27-7.34 (m, 5H), 7.22 (dd, 1H), 7.05 (dt, 1H), 5.43 (br, 1H), 3.76 (dd, 1H), 3.61 (dd, 1H), 1.83 (m, 1H), 1.68 (m, 1H), 1.41 (s, 3H), 0.75 (t, 3H) |
| 1-14 | 7.81 (dd, 1H), 7.30-7.35 (m, 5H), 7.22 (dd, 1H), 7.06 (dt, 1H), 5.34 (br, 1H), 3.75 (d, 2H), 1.78 (m, 4H), 0.81 (t, 6H) |
| 1-53 | 7.70 (d, 1H), 7.58 (t, 1H), 7.53 (t, 1H), 7.46 (d, 1H), 7.40 (s, 1H), 7.39 (d, 1H), 7.30 (d, 1H), 5.86 (br, 1H), 3.71 (dd, 2H), 3.00 (t, 2H), 2.44 (s, 3H) |
| 1-59 | 7.69 (d, 1H), 7.47-7.60 (m, 3H), 7.36 (t, 2H), 7.24 (d, 1H), 7.15 (t, 1H), 7.00-7.03 (m, 3H), 6.88 (dd, 1H), 5.85 (br, 1H), 3.73 (q, 2H), 3.05 (t, 2H) |

The endoparasite control agent of the present invention has excellent anti-endoparasite effect, and exerts appropriate control effect against endoparasites. The animal for which the endoparasite control agent of the present invention can be used is a human and an animal of non-human mammalian or avian species. Exemplary members of the non-human mammalian species include domestic animals, such as pigs, horses, cattle, sheep, goats, rabbits, camels, water buffalos, deer, mink and chinchillas; pet animals, such as dogs, cats, little birds and monkeys; and experimental animals, such as rats, mice, golden hamsters and guinea pigs. Exemplary members of the avian species include domestic fowls, such as chickens, ducks, aigamo ducks (crossbreeds of wild and domestic ducks), quails, domestic ducks, geese and turkeys.

Human endoparasites against which the endoparasite control agent of the present invention is effective are roughly classified into protozoa and helminths. Examples of the protozoa include, but are not limited thereto, Rhizopoda, such as *Entamoeba histolytica*; Mastigophora, such as *Leishmania*, *Trypanosoma* and *Trichomonas*; Sporozoea, such as *Plasmodium* and *Toxoplasma*; and Ciliophora, such as *Balantidium coli*. Examples of the helminths include, but are not limited thereto, Nematoda, such as *Ascaris lumbricoides*, *Anisakis*, *Toxocara canis*, *Trichostrongylus* spp., *Enterobius vermicularis*, hookworms (for example, *Ancylostoma duodenale*, *Necator americanus*, *Ancylostoma braziliense*, etc.), *Angiostrongylus* spp., *Gnathostoma* spp., filarial worms (filaria, *Wuchereria bancrofti*, *Brugia malayi*, etc.), *Onchocerca volvulus*, *Dracunculus medinensis*, *Trichinella spiralis* and *Strongyloides stercoralis*; Acanthocephala, such as *Macracanthorhynchus hirudinaceus*; Gordiacea, such as Gordioidea; Hirudinea, such as *Hirudo nipponia*; Trematoda, such as *Schistosoma japonicum*, *Schistosoma mansoni*, *Schistosoma haematobium*, *Clonorchis sinensis*, *Heterophyes heterophyes*, *Fasciola* spp. and *Paragonimus* spp.; and Cestoda, such as *Diphyllobothrium latum*, *Sparganum mansoni*, *Sparganum proliferum*, *Diplogonoporus grandis*, Taeniidae (for example, *Taeniarhynchus saginatus*, *Taenia solium*, *Echinococcus*, etc.), *Hymenolepis* spp., *Dipylidium caninum*, *Mesocestoides lineatus*, *Bertiella* spp. and *Nybelinia surmenicola*.

Non-human mammalian or avian endoparasites against which the endoparasite control agent of the present invention is effective are roughly classified into protozoa and helminths. Examples of the protozoa include, but are not limited thereto, Apicomplexa, such as Coccidia (for example, *Eimeria*, *Isospora*, *Toxoplasma*, *Neospora*, *Sarcocystis*, *Besnoitia*, *Hammondia*, *Cryptosporidium*, *Caryospora*, etc.), Haemosporina (for example, *Leucocytozoon*, *Plasmodium*, etc.), Piroplasma (for example, *Theileria*, *Anaplasma*, *Eperythrozoon*, *Haemobartonella*, *Ehrlichia*, etc.), and others (for example, *Hepatozoon*, *Haemogregarina*, etc.); Microspora, such as *Encephalitozoon* and *Nosema*; Mastigophora, such as Trypanosomatina (for example, *Trypanosoma*, *Leishmania*, etc.), Trichomonadida (for example, *Chilomastix*, *Trichomonas*, *Monocercomonas*, *Histomonas*, etc.), and Diplomonadida (for example, *Hexamita*, *Giardia*, etc.); Sarcodina, such as Amoebida (for example, *Entamoeba histolytica* (*Entamoeba*) etc.); and Ciliophora, such as *Balantidium coli* (*Balantidium*), *Buxtonella* and *Entodinium*.

Examples of the helminths include, but are not limited thereto, Nematoda, such as Ascaridida (for example, *Ascaris suum* (*Ascaris*), *Toxocara canis* and *Toxocara cati* (*Toxocara*), *Toxascaris leonina* (*Toxascaris*), *Parascaris equorum* (*Parascaris*), *Ascaridia galli* (*Ascaridia*), *Heterakis gallinarum* (*Heterakis*), *Anisakis*, etc.), Oxyurida (for example, *Oxyuris equi* (*Oxyuris*), *Passalurus ambiguus* (*Passalurus*), etc.), Strongylida (for example, *Strongylus vulgaris* (*Strongylus*), *Haemonchus contortus* (*Haemonchus*), *Ostertagia ostertagi* (*Ostertagia*), *Trichostrongylus colubriformis* (*Trichostrongylus*), *Cooperia punctata* (*Cooperia*), *Nematodirus filicollis* (*Nematodirus*), *Hyostrongylus rubidus* (*Hyostrongylus*), *Oesophagostomum radiatum* (*Oesophagostomum*), *Chabertia ovina* (*Chabertia*), *Ancylostoma caninum* (*Ancylostoma*), *Uncinaria stenocephala* (*Uncinaria*), *Necator americanus* (*Necator*), *Bunostomum phlebotomum* (*Bunostomum*), *Dictyocaulus viviparus* (*Dictyocaulus*), *Metastrongylus elongatus* (*Metastrongylus*), *Filaroides hirthi* (*Filaroides*), *Aelurostrongylus abstrusus* (*Aelurostrongylus*), *Angiostrongylus cantonensis* (*Angiostrongylus*), *Syngamus trachea* (*Syngamus*), *Stephanurus dentatus* (*Stephanurus*), etc.), Rhabditida (for example, *Strongyloides stercoralis* (*Strongyloides*), *Micronema*, etc.), Spirurida (for example, *Thelazia rhodesi* (*Thelazia*), *Oxyspirura mansoni* (*Oxyspirura*), *Spirocerca lupi* (*Spirocerca), *Gongylonema pulchrum* (*Gongylonema*), *Draschia megastoma* (*Draschia*), *Habronema microstoma* (*Habronema*), *Ascarops strongylina* (*Ascarops*), *Physaloptera praeputialis* (*Physaloptera*), *Gnathostoma spinigerum* (*Gnathostoma*), etc.), Filariida (for example, *Dirofilaria immitis* (*Dirofilaria*), *Setaria equina* (*Setaria*), *Dipetalonema, Parafilaria multipapillosa* (*Parafilaria*), *Onchocerca cervicalis* (*Onchocerca*), etc.), and Enoplida (for example, *Parafilaria bovicola* (*Parafilaria*), *Stephanofilaria okinawaensis* (*Stephanofilaria*), *Trichuris vulpis* (*Trichuris*), *Capillaria bovis* (*Capillaria*), *Trichosomoides crassicauda* (*Trichosomoides*), *Trichinella spiralis* (*Trichinella*), *Dioctophyma renale* (*Dioctophyma*), etc.); Trematoda, such as Fasciolata (for example, *Fasciola hepatica* (*Fasciola*), *Fasciolopsis buski* (*Fasciolopsis*), etc.), Paramphistomatidae (for example, *Homalogaster paloniae* (*Homalogaster*), etc.), Dicrocoelata (for example, *Eurytrema pancreaticum* (*Eurytrema*), *Dicrocoelium dendriticum* (*Dicrocoelium*), etc.), Diplostomata (for example, *Pharyngostomum cordatum* (*Pharyngostomum*), *Alaria*, etc.), Echinostomata (for example, *Echinostoma hortense* (*Echinostoma*), *Echinochasmus*, etc.), Troglotrematoidea (for example, lung flukes (*Paragonimus*), *Nanophyetus salmincola* (*Nanophyetus*), etc.), Opisthorchiida (for example, *Clonorchis sinensis* (*Clonorchis*) etc.), Heterophyida (for example, *Heterophyes heterophyes* (*Heterophyes*), *Metagonimus yokogawai* (*Metagonimus*), etc.), Plagiorchiida (for example, *Prosthogonimus ovatus* (*Prosthogonimus*) etc.), and Schistosomatidae (for example, *Schistosoma japonicum* (*Schistosoma*) etc.); Cestoda, such as Pseudophyllidea (for example, *Diphyllobothrium nihonkaiense* (*Diphyllobothrium*), *Spirometra erinacei* (*Spirometra*), etc.), and Cyclophyllidea (for example, *Anoplocephala perfoliata* (*Anoplocephala*), *Paranoplocephala mamillana* (*Paranoplocephala*), *Moniezia benedeni* (*Moniezia*), *Dipylidium caninum* (*Dipylidium*), *Mesocestoides lineatus* (*Mesocestoides*), *Taenia pisiformis* and *Taenia hydatigena* (*Taenia*), *Hydatigera taeniaeformis* (*Hydatigera*), *Multiceps multiceps* (*Multiceps*), *Echinococcus granulosus* (*Echinococcus*), *Echinococcus multilocularis* (*Echinococcus*), *Taenia solium* (*Taenia*), *Taeniarhynchus saginatus* (*Taeniarhynchus*), *Hymenolepis diminuta* (*Hymenolepis*), *Vampirolepis nana* (*Vampirolepis*), *Raillietina tetragona* (*Raillietina*), *Amoebotaenia sphenoides* (*Amoebotaenia*), etc.); Acanthocephala, such as *Macracanthorhynchus hirudinaceus* (*Macracanthorhynchus*) and *Moniliformis moniliformis* (*Moniliformis*); Linguatulida, such as *Linguatula serrata* (*Linguatula*); and other various parasites.

In different designations, examples of the helminths include, but are not limited to, Nematoda, such as Enoplida (for example, *Trichuris* spp., *Capillaria* spp., *Trichomosoides* spp., *Trichinella* spp., etc.), Rhabditia (for example, *Micronema* spp., *Strongyloides* spp., etc.), Strongylida (for example, *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp., etc.), Oxyurida (for example, *Oxyuris* spp., *Enterobius* spp., *Passalurus* spp., *Syphacia* spp., *Aspiculuris* spp., *Heterakis* spp., etc.), Ascaridia (for example, *Ascaris* spp., *Toxascaris* spp., *Toxocara* spp., *Parascaris* spp., *Anisakis* spp., *Ascaridia* spp., etc.), Spirurida (for example, *Gnathostoma* spp., *Physaloptera* spp., *Thelazia* spp., *Gongylonema* spp., *Habronema* spp., *Parabronema* spp., *Draschia* spp., *Dracunculus* spp., etc.), and Filariida (for example, *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., etc.); Acanthocephala (for example, *Filicollis* spp., *Moniliformis* spp., *Macracanthorhynchus* spp., *Prosthenorchis* spp., etc.); Trematoda including subclasses, such as Monogenea (for example, *Gyrodactylus* spp., *Dactylogyrus* spp., *Polystoma* spp., etc.) and Digenea (for example, *Diplostomum* spp., *Posthodiplostomum* spp., *Schistosoma* spp., *Trichobilharzia* spp., *Ornithbilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantoctyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp., etc.); Cestoda, such as Pseudophyllidea (for example, *Diphyllobothrium* spp., *Spirometra* spp., *Schistocephalus* spp., *Ligula* spp., *Bothridium* spp., *Diplogonoporus* spp., etc.), and Cyclophyllidea (for example, *Mesocestoides* spp., *Anoplocephala* spp., *Paranoplocehala* spp., *Moniezia* spp., *Thysanosomsa* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp., etc.); and others including parasites belonging to Acanthocephala and Linguatulida.

The endoparasite control agent of the present invention is effective against not only parasites that live in the body of an intermediate or final host, but also parasites that live in the body of a reservoir host. The compound represented by the general formula (I) of the present invention is effective at every developmental stage of parasites. For example, in the case of protozoa, the compound is effective against their cysts, precystic forms and trophozoites; schizonts and amoeboid forms at the asexual stage; gametocytes, gametes and zygotes at the sexual stage; sporozoites; etc. In the case of nematodes, the compound is effective against their eggs, larvae, and adults. The compound of the present invention is capable of not only combating parasites in the living body, but also even preventing parasitic infection by application to the environment as a route of infection. For example, soil-borne infection, i.e. infection from soil of crop fields and parks; percutaneous infection from water in rivers, lakes, marshes, paddy fields, etc.; oral infection from feces of animals such as dogs and cats; oral infection from saltwater fish, freshwater fish, crustaceans, shellfish, raw meat of domestic animals, etc.; infection from mosquitoes, gadflies, flies, cockroaches, mites, fleas, lice, assassin bugs, trombiculid mites, etc.; and the like can be prevented from occurring.

The endoparasite control agent of the present invention can be administered as a pharmaceutical for treatment or prevention of parasitosis in humans and animals of non-human mammalian or avian species. The mode of administration may be oral or parenteral administration. In the case of oral administration, the endoparasite control agent of the present invention can be administered, for example, as a capsule, a tablet, a pill, a powder, a granule, a fine granule, a powder, a syrup, an enteric-coated preparation, a suspension or a paste, or after blended in a liquid drink or feed for animals. In the case of parenteral administration, the endoparasite control agent of the present invention can be administered in a dosage form which allows sustained mucosal or percutaneous absorption, for example, as an injection, an infusion, a suppository, an emulsion, a suspension, a drop, an ointment, a cream, a solution, a lotion, a spray, an aerosol, a cataplasm or a tape.

In the case where the endoparasite control agent of the present invention is used as a pharmaceutical for humans and animals of non-human mammalian or avian species, the optimum amount (effective amount) of the active ingredient varies with the purpose (treatment or prevention), the kind of infectious parasite, the type and severity of infection, the dosage form, etc., but in general, the oral daily dose is in the range of about 0.0001 to 10000 mg/kg body weight and the parenteral daily dose is in the range of about 0.0001 to 10000 mg/kg body weight, and such a dose may be administered as a single dose or divided doses.

The concentration of the active ingredient in the endoparasite control agent of the present invention is generally about 0.001 to 100% by mass, preferably about 0.001 to 99% by mass, and more preferably about 0.005 to 20% by mass. The endoparasite control agent of the present invention may be a composition that can be directly administered, or a highly concentrated composition that is used for administration after diluted to a suitable concentration.

For the purpose of reinforcing or complementing the effect of the endoparasite control agent of the present invention, a combined use with any existing endoparasite control agent is possible. In such a combined use, two or more active ingredients may be mixed and formulated into a preparation before administration, or two or more different preparations may be administered separately.

EXAMPLES

Next, the present invention will be illustrated in detail by formulation examples and test examples of the endoparasite control agent of the present invention, but the scope of the present invention is not limited by the following formulation examples and test examples.

Formulation Example 1

Emulsion

Ten parts of the carboxamide derivative represented by the general formula (I) of the present invention, 6 parts of Sorpol 355S (surfactant, manufactured by Toho Chemical Industry), and 84 parts of Solves so 150 (manufactured by Exxon) are uniformly mixed with stirring to give an emulsion.

Formulation Example 2

Ointment

One part of the carboxamide derivative represented by the general formula (I) of the present invention, 50 parts of white beeswax, and 49 parts of white petrolatum are well mixed to give an ointment.

Formulation Example 3

Tablet

Two parts of the carboxamide derivative represented by the general formula (I) of the present invention, 10 parts of vegetable oil (olive oil), 3 parts of crystalline cellulose, 20 parts of white carbon, and 65 parts of kaolin are well mixed and compressed into a tablet.

Formulation Example 4

Injection

Ten parts of the carboxamide derivative represented by the general formula (I) of the present invention, 10 parts of propylene glycol for use as a food additive, and 80 parts of vegetable oil (corn oil) are mixed to give an injection.

Formulation Example 5

Solution

Five parts of the carboxamide derivative represented by the general formula (I) of the present invention, 20 parts of surfactant, and 75 parts of ion exchanged water are well mixed to give a solution.

Test Example 1

In Vitro Measurement of Inhibitory Activity on *Ascaris suum* Succinate-Ubiquinone Reductase (Mitochondrial Complex II)

To a solution containing 50 mM potassium phosphate (pH 7.4) and 0.1% (w/v) sucrose monolaurate, an electron acceptor ubiquinone-2 ($UQ_2$) was added at a final concentration of 60 µM, and the mixture was allowed to stand at 25° C. for 20 minutes. To this, potassium cyanide (final concentration: 2 mM) and mitochondria prepared from adult *Ascaris suum* muscle were added, and thorough mixing was done. To aliquots of the mixture, an inhibitor to be tested was added at various concentrations, and the mixtures were allowed to stand at 25° C. for 3 minutes. The enzymatic reaction was initiated by addition of potassium succinate (final concentration: 10 mM). The enzymatic activity was calculated based on the measurement of change in the absorbance at 278 nm of $UQ_2$ ($\epsilon=1.5\times10^4$ $M^{-1}$ $cm^{-1}$), and $IC_{50}$ was determined from the plot of the inhibition percentage against the inhibitor concentration.

Test Example 2

In Vitro Measurement of Inhibitory Activity on Porcine Succinate-Ubiquinone Reductase (Mitochondrial Complex II)

To a solution containing 50 mM potassium phosphate (pH 7.4) and 0.1% (w/v) sucrose monolaurate, an electron acceptor ubiquinone-2 ($UQ_2$) was added at a final concentration of 60 μM, and the mixture was allowed to stand at 25° C. for 20 minutes. To this, potassium cyanide (final concentration: 2 mM) and mitochondria prepared from porcine heart muscle were added, and thorough mixing was done. To aliquots of the mixture, an inhibitor to be tested was added at various concentrations, and the mixtures were allowed to stand at 25° C. for 3 minutes. The enzymatic reaction was initiated by addition of potassium succinate (final concentration: 10 mM). The enzymatic activity was calculated based on the measurement of change in the absorbance at 278 nm of $UQ_2$ ($\epsilon=1.5\times10^4$ $M^{-1}$ $cm^{-1}$), and $IC_{50}$ was determined from the plot of the inhibition percentage against the inhibitor concentration.

The results are shown in Table 5. In the table, "-" indicates "not tested," and "*Ascaris suum* $IC_{50}$ value (A)" indicates an $IC_{50}$ value (50% inhibitory concentration) for inhibition of succinate-ubiquinone reductase (mitochondrial complex II) of *Ascaris suum*. From the extent of inhibition of this respiratory enzyme, the parasite control activity can be estimated. "Porcine mitochondria $IC_{50}$ value (B)" indicates an $IC_{50}$ value for inhibition of succinate-ubiquinone reductase (mitochondrial complex II) of the host pig. From the extent of inhibition of this respiratory enzyme, the influence on the host can be estimated. A greater selectivity index B/A indicates a higher safety for the host.

TABLE 6

| Compound No. | *Ascaris suum* $IC_{50}$ value(A) | Porcine mitochondria $IC_{50}$ value(B) | Selectivity B/A |
| --- | --- | --- | --- |
| 1-3 | 1.21 nM | no inhibition at 90 μM | >27000 |
| 1-16 | 3.34 nM | no inhibition at 90 μM | >74400 |
| 1-27 | 1.69 nM | no inhibition at 90 μM | >53300 |
| 1-32 | 2.15 nM | no inhibition at 9 μM | >4190 |
| 1-64 | 9 nM | no inhibition at 9 μM | >9150 |
| 1-81 | 4.8 nM | 10% at 90 μM | >18800 |
| 1-88 | 12 nM | — | Not calculated |
| 1-110 | 4.07 nM | no inhibition at 10 μM | >2460 |
| 1-111 | 13.1 nM | no inhibition at 90 μM | >6870 |
| 1-112 | 1.50 nM | no inhibition at 90 μM | >60000 |
| 2-1 | 5.47 nM | 111 μM | 20295 |
| 2-3 | 127 nM | no inhibition at 90 μM | >709 |
| 2-4 | 70.5 nM | no inhibition at 90 μM | >1280 |
| 2-5 | 3.83 nM | no inhibition at 9 μM | >2350 |
| 2-6 | 28.3 nM | 10% at 90 μM | >3180 |
| 2-7 | 14 nM | no inhibition at 90 μM | >6430 |
| 2-8 | 38.2 nM | no inhibition at 90 μM | >2360 |
| 3-7 | 1.60 nM | 90 μM | 56250 |
| 4-1 | 3.44 nM | — | Not calculated |
| 4-2 | 5.15 nM | — | Not calculated |
| 4-3 | 1.98 nM | — | Not calculated |
| 4-4 | 8.36 nM | 16% at 90 μM | >10770 |
| 4-5 | 6.07 nM | 11% at 90 μM | >14830 |
| 4-6 | 8.34 nM | no inhibition at 9 μM | >1079 |
| 4-7 | 1.78 nM | 103 μM | 57870 |
| 4-8 | 2.61 nM | 5% at 9 μM | >3448 |

As is clear from the results in Table 5, the carboxamide derivatives represented by the general formula (I) of the present invention and salts thereof showed a strong inhibitory activity on the parasitic succinate-ubiquinone reductase (mitochondrial complex II) ($IC_{50}$ values: 1.21 to 127 nM), but hardly affected the activity of succinate-ubiquinone reductase (mitochondrial complex II) of the host pig (more than 1.000-fold selectivity). Therefore, the endoparasite control agent of the present invention is not only highly active in parasite control, but also highly safe for the host.

Test Example 3

In Vivo Activity on *Haemonchus contortus*

The test was conducted according to the larval migration inhibition assay (LMIA: Demeler et al., 2010). A larval suspension was prepared so as to contain 100 to 120 third-stage larvae of *Haemonchus contortus* per 20 μL, and then 20 μL of the larval suspension was added to each well on a breeding plate to which compound solutions adjusted to predetermined concentrations were previously added at 1780 μL/well each. The breeding plate was maintained for breeding at 28° C. for 24 hours. Meanwhile, to a plate for larval migration observation, 400 μL of a 1.5% agar solution was added and left to stand until coagulation. Then, the larvae were allowed to migrate through a sieve from the breeding plate to the plate for larval migration observation, and the plates were maintained for breeding at 28° C. for another 24 hours. The larvae which had migrated, and the larvae which had not migrated were counted, the percentage of migration inhibition was calculated, and the activity was graded based on the following criterion. All samples were tested in duplicate, and the results are shown in Table 7. In the table, "-" indicates "not tested."
Percentage of Migration Inhibition
70 to 100%: A
40 to 69%: B
10 to 39%: C
lower than 10%: D

TABLE 7

| Compound No. | Concentration (ppm) | | | |
| --- | --- | --- | --- | --- |
| | 100 | 10 | 1 | 0.1 |
| 1-16 | B | C | C | C |
| 1-32 | — | B | C | C |
| 2-1 | — | — | B | C |
| 2-6 | — | C | C | C |
| 3-7 | B | C | C | C |
| 4-1 | — | C | C | C |
| 4-7 | B | C | C | C |

As is clear from the results in Table 7, the compounds proven in the above-described in vitro test to have a strong activity showed a strong activity in the in vivo test as well, and thus the compound of the present invention is effective as an endoparasite control agent.

The invention claimed is:

1. A method for controlling endoparasites, wherein the endoparasite is selected from the subclass Rhabditia or Spiruria, in a mammal or bird, comprising orally or parenterally administering an effective amount of the endoparasite control agent comprising a carboxamide derivative represented by the general formula(I):

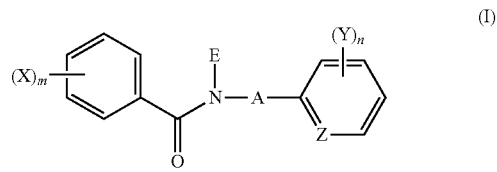

wherein A represents a ($C_1$-$C_2$) alkylene group which is optionally substituted by a ($C_1$-$C_6$) alkyl group and/or a ($C_3$-$C_6$) cycloalkyl group E represents a hydrogen atom, each X may be the same or different, and represents a halogen atom; or a ($C_1$-$C_6$) alkyl group optionally substituted by a halogen atom;

m represents an integer of 0, 1 or 2, each Y may be the same or different, and represents a halogen atom; a ($C_1$-$C_6$) alkyl group optionally substituted by a halogen atom;

n represents an integer of 0, 1, 2 or 3 and

Z represents CH; or CY (wherein Y is as defined above), or a salt thereof as an active ingredient to said mammal or a bird.

2. The method according to claim 1, wherein an effective amount of the endoparasite control agent is administered to a mammal.

3. The method according to claim 2, wherein the mammal is a domestic animal.

4. The method according to claim 2, wherein the mammal is human.

5. The method according to claim 1, wherein m represents 1 or 2.

6. The method according to claim 1, wherein m represents 1, each Y may be the same or different, and represents a halogen atom or a ($C_1$-$C_6$)alkyl group optionally substituted by a halogen atom, and n represents an integer of 1 to 3.

7. The method according to claim 1, wherein the carboxamide derivative represented by the general formula (I) is a compound of the formula:

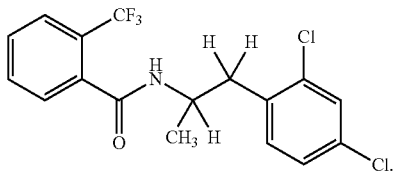

8. The method according to claim 1, wherein the endoparasite is *Haemonchus contortus*.

* * * * *

UNITED STATES PATENT AND TRADEMARK OFFICE
CERTIFICATE OF CORRECTION

| | |
|---|---|
| PATENT NO. | : 9,447,042 B2 |
| APPLICATION NO. | : 14/000974 |
| DATED | : September 20, 2016 |
| INVENTOR(S) | : Kiyoshi Kita et al. |

Page 1 of 1

It is certified that error appears in the above-identified patent and that said Letters Patent is hereby corrected as shown below:

In the Claims

At Column 24, Lines 49-51, "wherein the endoparasite is selected from the subclass Rhabditia or Spiruria, in a mammal or bird," should be -- in a mammal or bird, wherein the endoparasite is selected from the subclass Rhabditia or Spiruria, --.

At Column 24, Line 67, "group" should be -- group, --.

At Column 26, Line 4, "(C1-C6)alkyl" should be -- (C1-C6) alkyl --.

Signed and Sealed this
Seventh Day of March, 2017

Michelle K. Lee
*Director of the United States Patent and Trademark Office*